United States Patent
Khimulya et al.

(10) Patent No.: US 12,040,050 B1
(45) Date of Patent: Jul. 16, 2024

(54) SYSTEMS AND METHODS FOR RATIONAL PROTEIN ENGINEERING WITH DEEP REPRESENTATION LEARNING

(71) Applicants: Grigory Khimulya, Cambridge, MA (US); Ethan Alley, Albuquerque, NM (US); Surojit Biswas, Boston, MA (US)

(72) Inventors: Grigory Khimulya, Cambridge, MA (US); Ethan Alley, Albuquerque, NM (US); Surojit Biswas, Boston, MA (US)

(73) Assignee: NABLA BIO, INC., Cambridge, MA (US)

( * ) Notice: Subject to any disclaimer, the term of this patent is extended or adjusted under 35 U.S.C. 154(b) by 1047 days.

(21) Appl. No.: 16/812,111

(22) Filed: Mar. 6, 2020

Related U.S. Application Data

(60) Provisional application No. 62/814,394, filed on Mar. 6, 2019.

(51) Int. Cl.

| | |
|---|---|
| *G06N 3/08* | (2023.01) |
| *G06N 3/0442* | (2023.01) |
| *G06N 3/045* | (2023.01) |
| *G06N 3/084* | (2023.01) |
| *G06N 3/088* | (2023.01) |
| *G16B 15/00* | (2019.01) |
| *G16B 20/00* | (2019.01) |
| *G16B 30/00* | (2019.01) |
| *G16B 35/00* | (2019.01) |

(Continued)

(52) U.S. Cl.
CPC ........... *G16B 30/00* (2019.02); *G06N 3/0442* (2023.01); *G06N 3/045* (2023.01); *G06N 3/084* (2013.01); *G06N 3/088* (2013.01); *G16B 15/00* (2019.02); *G16B 20/00* (2019.02); *G16B 35/00* (2019.02); *G16B 25/10* (2019.02); *G16B 50/00* (2019.02)

(58) Field of Classification Search
CPC ...... G06N 3/045; G06N 3/0455; G06N 3/084; G06N 3/088; G06N 3/08; G16B 30/00
See application file for complete search history.

(56) References Cited

U.S. PATENT DOCUMENTS

2019/0130212 A1\* 5/2019 Cheng ................. G06F 18/2137
2020/0082916 A1\* 3/2020 Polykovskiy ............ G06N 3/08
(Continued)

OTHER PUBLICATIONS

Krause, Ben, et al. "Multiplicative LSTM for sequence modelling." arXiv preprint arXiv:1609.07959 (2016). (Year: 2016).\*

(Continued)

*Primary Examiner* — Hal Schnee
(74) *Attorney, Agent, or Firm* — MODALITY LAW PLLC; Chang B. Hong

(57) ABSTRACT

A dataset describing a collection of proteins is loaded, which identifies, for each protein, a respective value of a characteristic of interest. The dataset is provided as one or more inputs to a trained unsupervised representation model to cause the trained unsupervised representation model to generate a representation for each protein in the collection. The representation for each protein is input into a supervised top model to train the supervised top model to obtain a predicted characteristic and the trained supervised top model is used to obtain a predicted characteristic for a particular protein.

20 Claims, 6 Drawing Sheets

(51) Int. Cl.
    *G16B 25/10*        (2019.01)
    *G16B 50/00*        (2019.01)

(56) References Cited

U.S. PATENT DOCUMENTS

2020/0273541 A1\*  8/2020  Costello ................. G16B 40/20
2022/0122692 A1\*  4/2022  Feala .................... G16B 40/20

OTHER PUBLICATIONS

Lyu, Xinrui, et al. "Improving clinical predictions through unsupervised time series representation learning." arXiv preprint arXiv:1812.00490 (2018). (Year: 2018).\*

Jaeger, Sabrina, Simone Fulle, and Samo Turk. "Mol2vec: unsupervised machine learning approach with chemical intuition." Journal of chemical information and modeling 58.1 (2018): 27-35. (Year: 2018).\*

Alley et al., Unified rational protein engineering with sequence-only deep representation learning bioRxiv 589333; doi: https://doi.org/10.1101/589333.

Alley, E.C., Khimulya, G., Biswas, S. et al. Unified rational protein engineering with sequence-based deep representation learning. Nat Methods 16, 1315-1322 (2019).

\* cited by examiner

Step 1: Training Unsupervised
Representation Model
125

Obtaining vector representation using trained
unsupervised representation model

SYSTEMS AND METHODS FOR RATIONAL PROTEIN ENGINEERING WITH DEEP REPRESENTATION LEARNING

RELATED APPLICATION

This application claims benefit to U.S. Provisional Patent Application Ser. No. 62/814,394, filed Mar. 6, 2019 and incorporated by reference herein in its entirety.

GOVERNMENT SUPPORT

The invention is supported, in whole or in part, by NIH Training Grant to the Harvard Bioinformatics and Integrative Genomics program. The Government may have certain rights in the invention.

FIELD OF THE INVENTION

The present invention relates to rational protein engineering. In particular, the present invention relates to systems and methods for rational protein engineering with deep representation learning.

BACKGROUND

Generally, protein engineering has utilized random mutagenesis, screening, and selection, or alternatively model-based rational design to develop new protein variants with novel, improved, or distinct function. Protein engineering has the potential to transform synthetic biology, medicine, and nanotechnology. Traditional approaches to protein engineering rely on random variation and screening/selection without modelling the relationship between sequence and function. In contrast, rational engineering approaches seek to build quantitative models of protein properties, and use these models to more efficiently traverse the fitness landscape to overcome the challenges of directed evolution. Such rational design involves a holistic and predictive understanding of structural stability and quantitative molecular function that has not been consolidated in a generalizable framework to date.

BRIEF DESCRIPTION OF THE FIGURES

These and other characteristics of the present disclosure will be more fully understood by reference to the following detailed description in conjunction with the attached drawings, in which.

DETAILED DESCRIPTION OF EXAMPLE EMBODIMENTS

Figure 1:
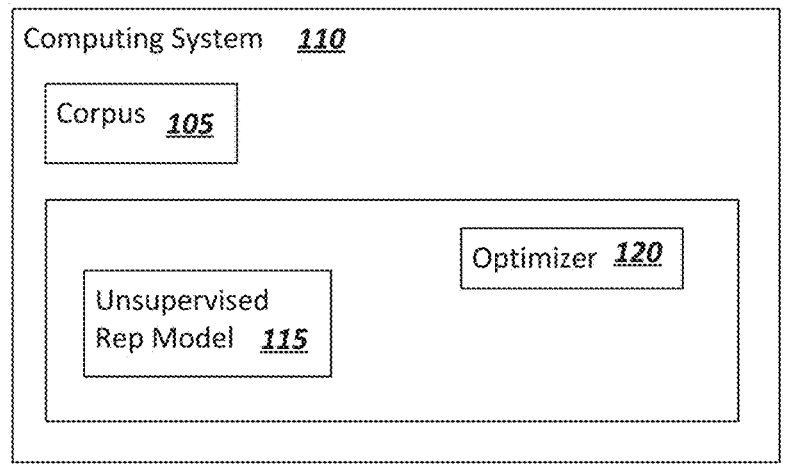
FIG. 1 is an exemplary process for training and utilizing an unsupervised representation model, in accordance with at least some embodiments.
Figure 1:
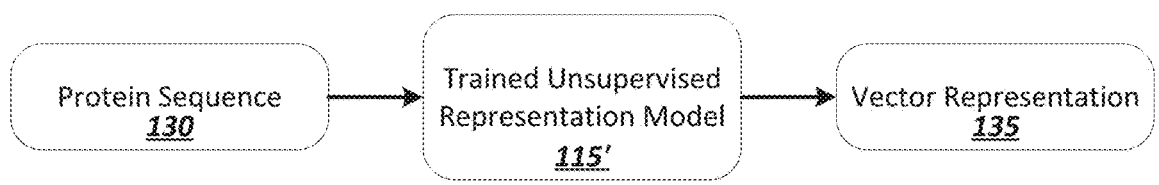

An illustrative embodiment relates an unsupervised deep representation learning model, which uses unlabeled protein data to learn to summarize fundamental protein characteristics, which can then be used to solve a variety of protein engineering problems as described below. There is a need for improvements for predicting stability of natural and de novo designed proteins as well as quantitative function of molecularly diverse mutants for, among other purposes, guiding the design of new and improved protein variants. The solutions described herein address these and other example needs, in addition to having other desirable characteristics.

FIGS. 1 through 6, wherein like parts are designated by like reference numerals throughout, illustrate an example embodiment or embodiments of improved operation for analyzing protein sequences, according to the present disclosure. Although the example solutions discussed herein will be described with reference to the example embodiment or embodiments illustrated in the figures, it should be understood that many alternative forms can embody such solutions. One of skill in the art will additionally appreciate different ways to alter the parameters of the embodiment(s) disclosed, such as the size, shape, or type of elements or materials, in a manner still in keeping with the spirit and scope of the present disclosure.

Referring to FIG. 1, in some embodiments, a process 100 for training and utilizing an unsupervised representation model is provided. Initially, a corpus 105 (collection) of protein sequences, preferably a large collection (over 20 million in our experiment), is provided. The collection can include all sequenced proteins available in public databases (such as https://www.uniprot.org). The collection can be cleaned from homologous sequences, making sure that proteins in the collection share at most X % sequence similarity with each other (for example, X=50, but can be anything). The homologous sequences can be cleaned using any combination of methods known in the art (for example, using the clustering with CD-HIT algorithm and representative sequence selection). In some embodiments, the collection can include a higher than random proportion of proteins which are closer to the proteins one wants to engineer, such as proteins with higher sequence similarity to the protein(s) one wants to engineer, similar function, similar biophysical parameters, similar expression patterns, similar evolutionary origin and others, such as the exemplary embodiments described herein.

In some embodiments, permissible models can be utilized by a computing system 110 with the process 100 as unsupervised representation models 115 to learn unsupervised representations of protein sequences. The permissible models can include a variety of artificial neural network architectures with at least one hidden layer, which can accept variable length sequences as input. These include without limitation models that contain a latent state as a fixed-length vector, such as Recurrent neural networks (RNNs), including long short-term memory networks (LSTMs), such as multiplicative (mLSTMs). Permissible models can also include other models which do not include latent state as a single fixed-length vector, for example a transformer architecture, such as GPT (Generative Pre-Training), Transformer-XL and BERT (Bidirectional Encoder Representations from Transformers), or a convolutional architecture, such as Temporal Convolutional Networks, among other examples.

Figure 6:
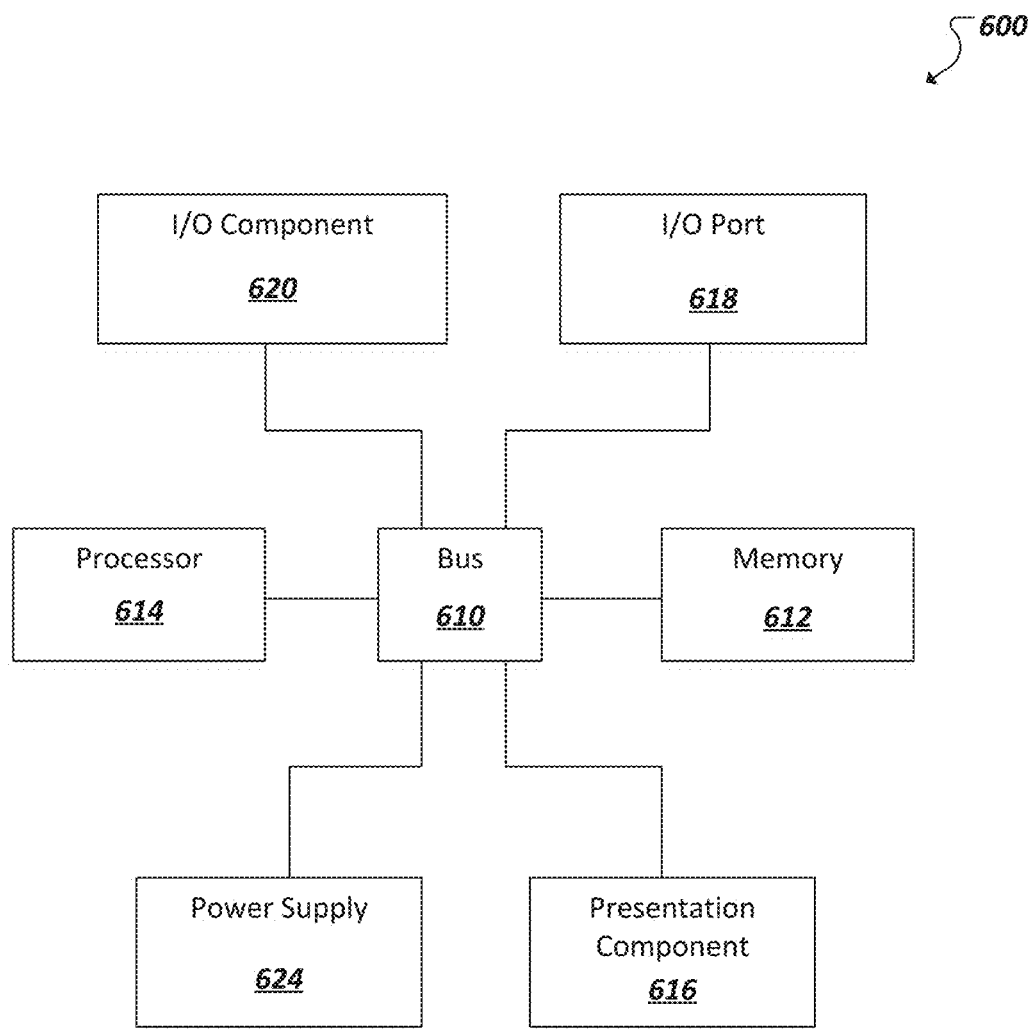
FIG. 6 is an exemplary computer architecture for implementing one or more of the described embodiments herein.

Continuing with FIG. 1, during training 125, protein sequences from corpus 105 can be processed by the model 115 one-by-one or in batches on a computer. The model 115 can utilize an optimizer 120 (implemented in hardware or software of the computing system 110) to optimize an objective based on the sequences it sees and optionally additional data, and trains to construct a useful internal latent state in the process. For example, the system 110 can include one or more processor devices (e.g., a central processing unit (CPU), graphics processing unit (GPU), tensor processing unit (TPU), etc., such as depicted in FIG. 6) and an optimizer 120 (e.g., stochastic gradient descent (SGD), Adam, etc.) In some embodiments, the optimizer 120 can use the loss (such as the measure of cross-entropy between the prediction and the actual next amino acid in the next amino acid prediction task) to update the internal parameters/weights of the model 115 to make it better at performing the task it is trained to perform. This procedure can work with a variety of tasks and losses, including a Generative Adversarial Network (GAN) loss optionally with improvements such as Wasserstein GAN, a masked language model-type loss (where the model attempts to reconstruct a missing (masked) amino acid or a block of amino acids in a protein sequence), a next amino acid prediction task with (for example) a cross-entropy loss, an autoencoder task and any other task/loss that does not require a labeled target variable.

In some embodiments, the model 115 can be trained 125 with two or more objective functions among the ones described for the models the above list references and/or additional objectives utilizing more data, such as 3-dimensional protein structure data (such as RGN (Recurrent Geometric Networks) objective), protein-level annotation data (such as predicting GeneOntology annotations), including categorical, binary, and/or quantitative annotations. In some embodiments, some or all of the latent states in the model 115 may be constrained by a prior, such as a gaussian prior to aid disentanglement of features and interpretability.

In some embodiments, an mLSTM model can serve as an unsupervised representation model 115. During training, it can go through each sequence amino acid by amino acid trying to predict the next amino acid based on the ones it has already seen. For example, such prediction can be done by inputting the one-hot-encoded sequence of amino acids the model 115 has seen so far into the model and utilizing the weights of the model neurons to compute a prediction of the next amino acid. The optimizer 120 (for example, Adam) can utilize a cross-entropy loss to update the trainable parameters of the mLSTM model as to make it perform better at this next-amino acid prediction task. In some embodiments, to speed up the training, the model can process sequences in batches on a GPU.

In some embodiments, the training can be stopped according to a variety of criteria—for example, when the loss stops improving for X iterations, or when the model has seen all the proteins in the collection X times. Optionally, the training process can be repeated with different hyperparameters to improve results. After that, in one embodiment, such as with the mLSTM model, the model's latent state for any protein sequence 130 can serve as a fixed length vector representation 135 (from now on "representation") for that protein (for example, in case of LSTM, the final hidden state, final cell state and average hidden state, as well as concatenations thereof can serve as representations, as described further herein). After this step, the trained unsupervised representation model 115' can be used to solve many different problems, for example, using the processes discussed with respect to FIGS. 2-4.

Figure 2:
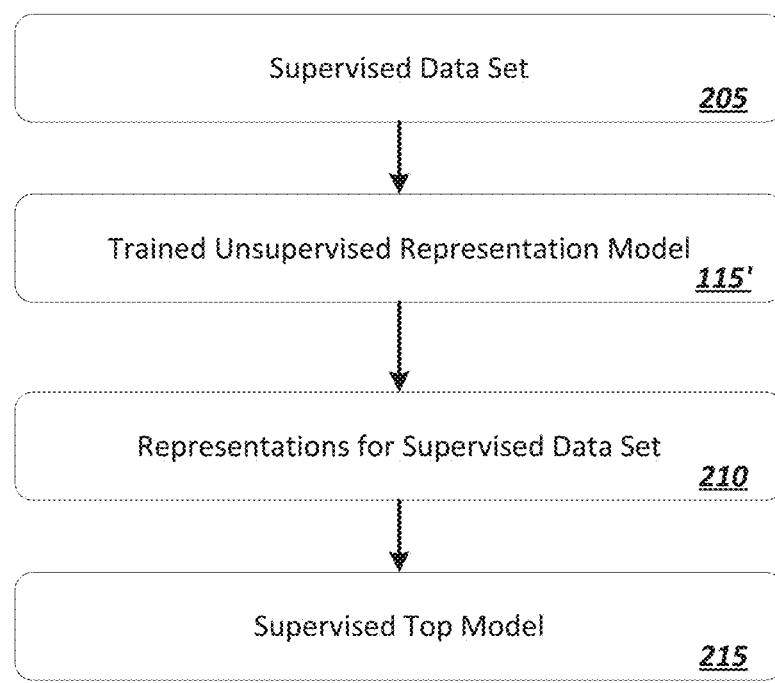
FIG. 2 is an exemplary process for protein characteristic/function prediction, in accordance with at least some embodiments.

Referring to FIG. 2, in some embodiments, some implementations can perform protein characteristic/function prediction to outperform competitive approaches on average 2× on a variety of protein characteristic/function prediction tasks. A characteristic can be anything that can be categorically, binarily or quantitatively measured about the protein. Characteristics include without limitation, stability (including thermal, acid-base, protease digestibility and other stability characteristics), function (including fluorescence, binding to ligands such as protein partners, organic and inorganic small molecules, and nucleic acids; catalysis and other functional characteristics), structural motifs or 3D structure, and biophysical characteristics, such as charge, solubility, and others.

Characteristic can also be a combination of two or more characteristics if one wants to predict/optimize multiple characteristics at the same time. In some embodiments, the process in FIG. 2 can utilized the trained unsupervised representation model 115' as obtained in FIG. 1. In some embodiments, the model can be "group fine-tuned" in order to obtain more effective representations for a particular protein/group of proteins the engineer is interested in. In some embodiments, a group are proteins that are evolutionarily related to the protein one would like to predict characteristics/function for can be utilized. The group fine tuning in that case consists of running the training procedure described with respect to FIG. 1 on a set of related sequences collected in an automated way, such as using a JackHMMER search tool. For example, in the case of optimizing characteristics of green fluorescent protein GFP, the group may include the proteins evolutionarily related or structurally or sequence-wise similar to GFP, such as described in the examples herein.

In some embodiments, a supervised dataset 205 can be utilized. The supervised dataset can include a collection of proteins with each protein annotated with a value of the characteristic of interest (for example, thermostability). Using the trained unsupervised representation model 115', one obtains a representation for each protein in the dataset based on its sequence as described in relation to FIG. 1. In some embodiments, a supervised top model can be utilized 215. The supervised top model 215 can be a trainable model that takes as input a representation of a protein (e.g., obtained as described using a trained unsupervised representation model) and outputs a predicted characteristic. In some embodiments, the supervised top model 215 can be a LASSO regression inputting a representation and utilizing its weight vector to compute a prediction for the characteristic of the represented protein sequence.

Continuing with FIG. 2, in some embodiments, the supervised top model 215 can be trained to predict the characteristic of interest using the supervised dataset 205 as a training dataset. During training, the supervised top model inputs representations for proteins in the training dataset and generates characteristic predictions for those utilizing its parameters and is trained by adjusting the supervised top model's parameters as to minimize as measure of prediction error compared to the corresponding values of the characteristic of interest. For a new protein of interest, the trained unsupervised representation model 115' can be used to get a representation 210 for that new protein. The representation for that new protein can be input into the trained supervised top model 215 to obtain the output-prediction of the protein characteristic of interest for the new protein.

In an alternative embodiment ("task finetuning"), trained unsupervised representation model can be utilized in full, with some or all of its parameters finetuned to a particular function/characteristic prediction task, such as classification or regression. For example, a supervised top model 215 such as a feed-forward network set up as to back propagate the loss to some or all of the trainable parameters of the unsupervised representation model can be trained to predict the characteristic/function on the supervised dataset, while also training the parameters of the underlying unsupervised representation model, or preferably as subset of those.

Figure 3:
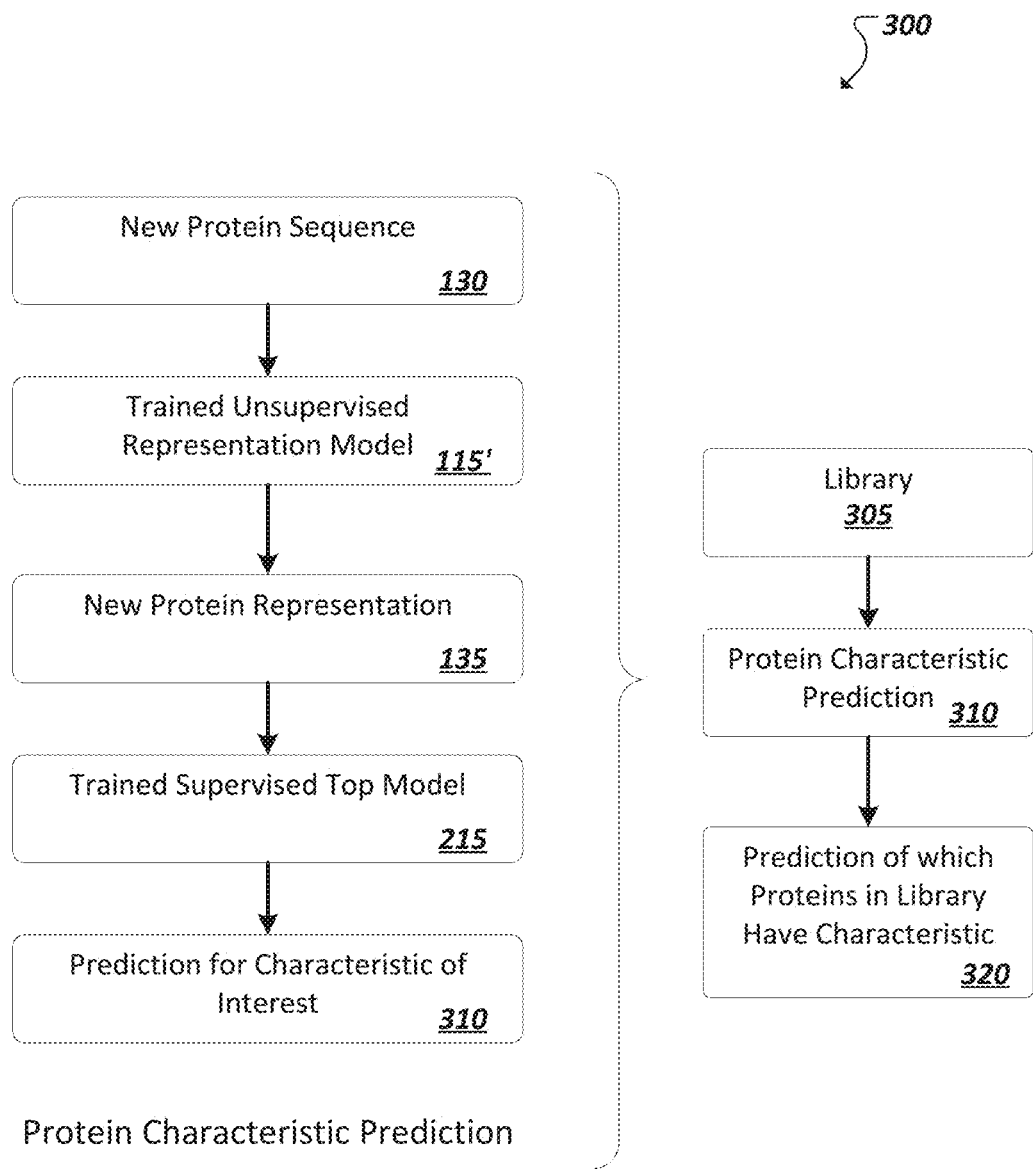
FIG. 3 is an exemplary process for protein characteristic engineering/optimization, in accordance with at least some embodiments.

Referring to FIG. 3, a process for protein characteristic engineering/optimization is provided. The process can be used for getting proteins with characteristic of interest (for example, high thermostability) and the process can achieve 100× lower costs of protein characteristic engineering/optimization compared to traditional Doc2Vec techniques. In some embodiments, the process of FIG. 3 can include similar features to that of FIGS. 1 and 2. In addition to those features, in some embodiments, the process can utilize a library 305 including a collection of protein sequences that may have the characteristic of interest. This collection can be prepared through many methods, including but not limited to random generation, identification of extant protein sequences using homology or other methods, biophysical protein design software, or the computational reconstruction of ancestral proteins from extant sequences.

Continuing with the process of FIG. 3, the steps in FIG. 1 can repeated to predict the value of the characteristic of interest 310 for each protein in the library. Proteins that are predicted to have the characteristic from FIG. 1 tend to actually have said characteristic. This allows one to save money and time by choosing to only synthesize and/or experimentally characterize the protein(s) (e.g., 320) from the library that are predicted to have the characteristic. The predictive model may be optionally combined with search algorithms to navigate a large library.

Figure 4:
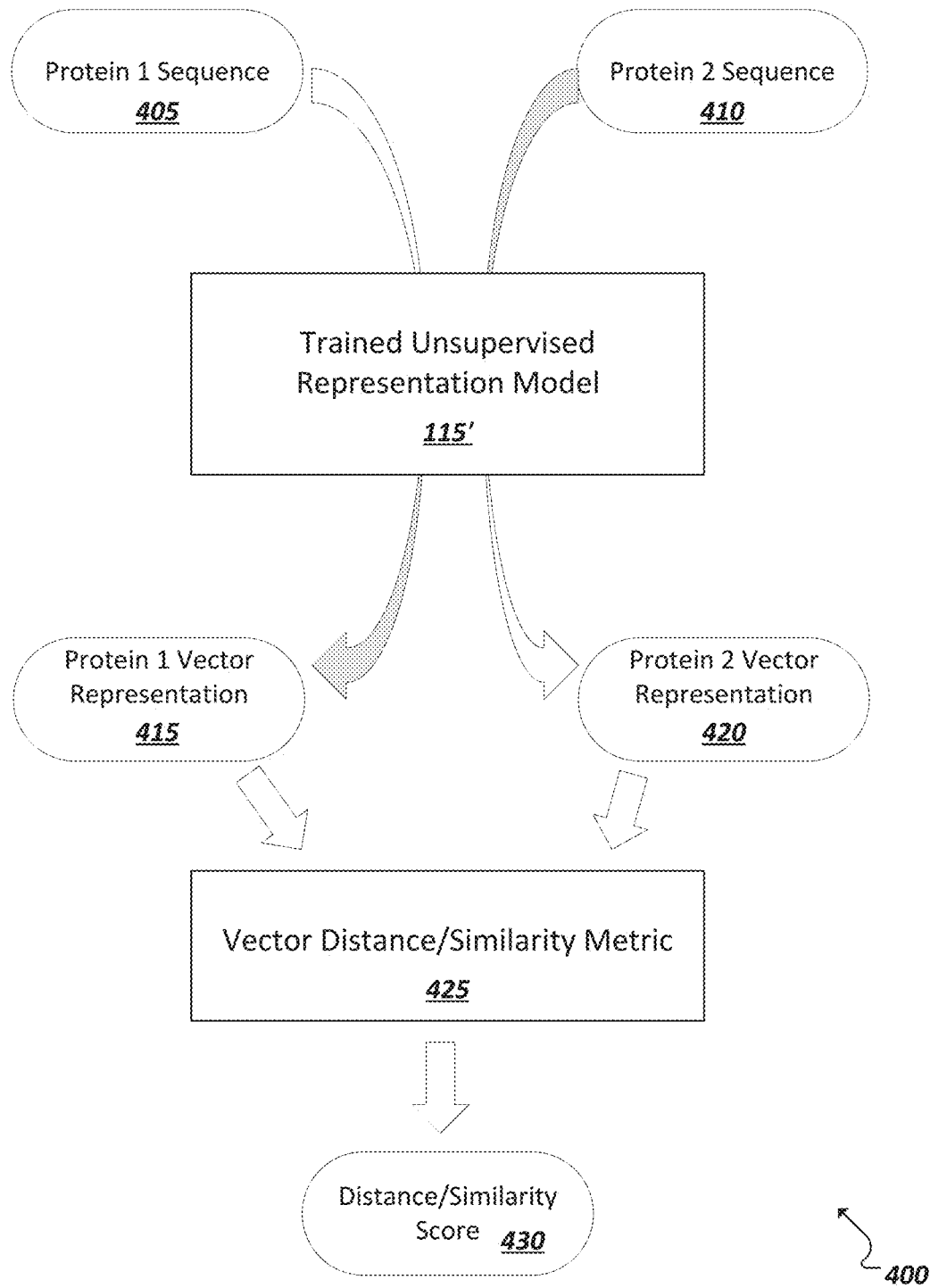
FIG. 4 is an exemplary process for protein homology detection, in accordance with at least some embodiments.

Referring to FIG. 4, a process for protein homology detection is provided. The process 400 can outperform PSI-BLAST and many other methods on two standard benchmarks (clarification: the benchmarks do not directly reconstruct real world usage, where the quality of homology detection is hard to quantify in practice, and instead provide a controlled estimate accepted in the field). The advantages of this approach include, for instance, fast computation enabled by parallelizable vector mathematics and ability to compare proteins whose sequences do not overlap enough for traditional homology detection methods to work. The steps for the process 400 for determining the degree of homology/similarity between protein 1 405 and protein 2 410 can include using trained unsupervised representation model 115' obtained using the process 100 discussed with respect to FIG. 1 and a sequence of protein 1 405 to obtain a representation 415 for protein 1. The process 400 can also include using trained unsupervised representation model 115' obtained during process 100, discussed with respect to FIG. 1 and a sequence of protein 2 410 to obtain a representation 420 for protein 2. The process 400 can further include using a vector distance or similarity metric solver 425 (e.g., Euclidean distance, cosine similarity, earth mover's distance) to obtain distance or similarity 430 between representations of protein 1 405 and protein 2 410. The proteins less distant from each other can be considered to be more similar/homologous.

Continuing with FIG. 4, in some embodiments, the process 400 can include steps for finding the closest proteins in a protein database to a given protein. That include steps for finding the closest proteins in a protein database to a given protein can include obtaining homology/similarity degree estimate for the given protein to each protein in the database as described in the procedure above, ranking proteins in the database by these homology/similarity degree estimates. As would be appreciated by one skilled in the art, in a large-scale system, the procedures above may be performed in advance of a search query as needed to speed up the search.

Figure 5:
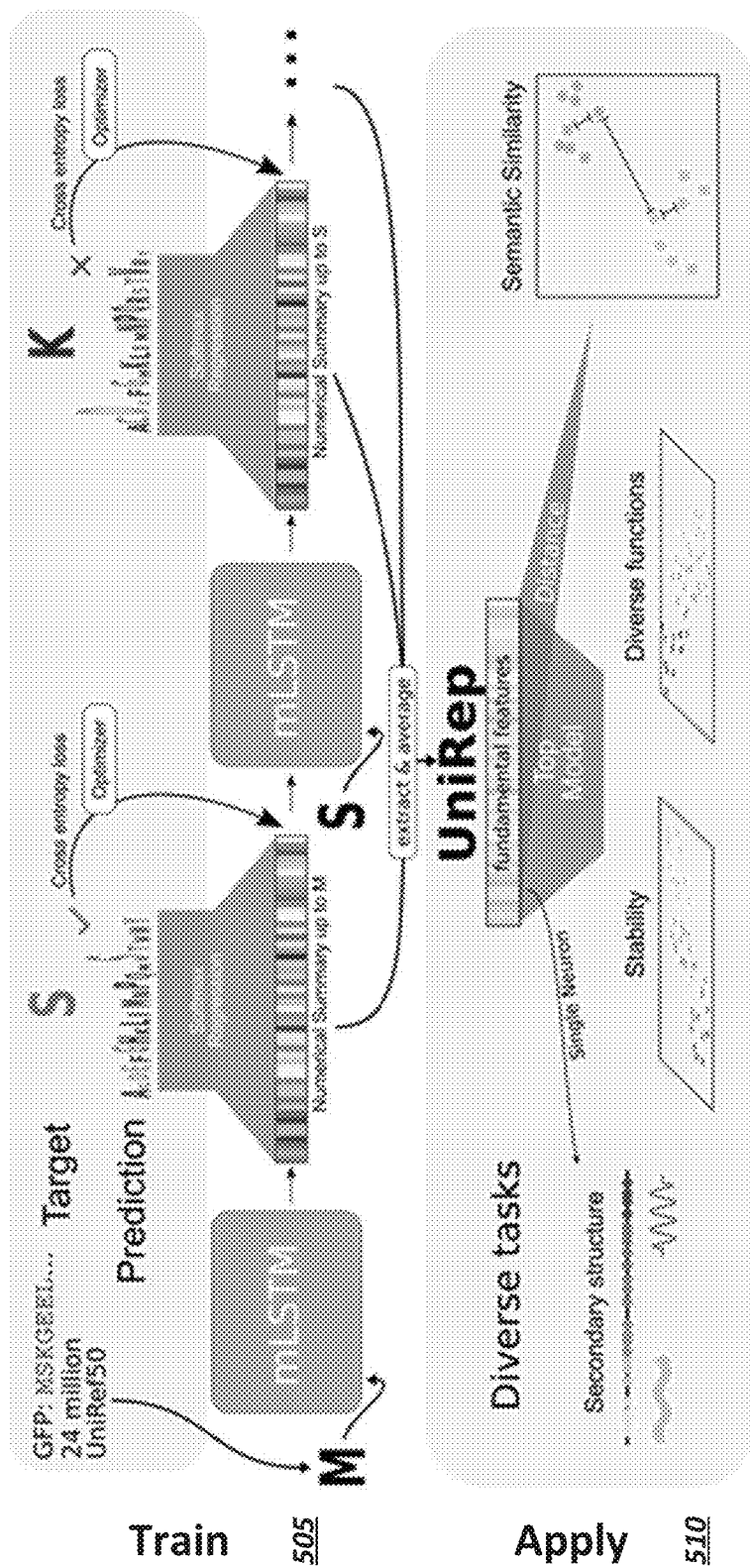
FIG. 5 is a block diagram illustrating an exemplary implementation of the training and application of an example unsupervised representation model.

There is a plethora of publicly available raw protein sequence data and the number of protein sequences described in such data is growing exponentially. While traditional models attempt to engage in model-based protein engineering and protein characteristic prediction, these traditional models fail to take advantage of the full scale of protein sequence databases, and thus do not perform well on a comprehensive comparative evaluation. As represented in FIG. 5, in an improved implementation, a recurrent neural network is used to learn statistical representations of proteins from ~24 million UniRef50 sequences (at 505). Without structural or evolutionary data, this unified representation (UniRep) summarizes arbitrary protein sequences into fixed-length vectors approximating fundamental protein features (at 510). Such a solution scalably leverages underutilized raw sequences to alleviate the data scarcity constraining protein informatics to date, and achieves generalizable, superior performance in critical engineering tasks from stability, to function, to design.

In one example implementation, an unsupervised representation model may be implemented utilizing Multiplicative Long-Short-Term-Memory (mLSTM) Recurrent Neural Networks (RNNs). An mLSTM-based representation model learns semantically rich representations from a massive protein sequence database. Such a model can learn rich representations for natural language which enable state-of-the-art performance on critical tasks. This architecture learns by going through a sequence of characters in order, trying to predict the next one based on the model's dynamic internal "summary" of the sequence it has seen so far (its "hidden state"). During training, the model gradually revises the way it constructs its hidden state in order to maximize the accuracy of its predictions, resulting in a progressively better statistical summary, or representation, of the sequence.

FIG. 5 illustrates a representation of the training and use of an example mLSTM-based representation model and shows an example workflow to learn and apply deep protein representations. For instance, an mLSTM-based representation model, such as the example UniRep model illustrated in FIG. 5, may be trained 505 on 24 million UniRef50 primary amino acid sequences. The model was trained to perform next amino acid prediction (minimizing cross-entropy loss), and in so doing, is forced to learn how to internally represent proteins. During application 510, the trained model is used to generate a single fixed-length vector representation of the input sequence by globally averaging intermediate mLSTM numerical summaries (the hidden states). A top model (e.g. a sparse linear regression or random forest) trained on top of the representation, is utilized to act as a featurization of the input sequence, enabling supervised learning on diverse protein informatics tasks.

In one example, after training the example mLSTM-based representation model (e.g., with amino acid character embeddings on ~24 million UniRef50 amino acid sequences for ~3 weeks on 4 Nvidia K80 GPUs), interrogation of the model and its internal state reveals that the amino-acid embeddings learned by UniRep contained physicochemically meaningful clusters. Indeed, UniRep features at the amino acid to whole proteome level may reveal that these features at least embody a subset of known characteristics of proteins with the possibility of UniRep representing more. For instance, because UniRep is learned from raw data, it is unconstrained by existing mental models for understanding proteins, and may therefore approximate currently unknown engineering-relevant features. Taken together, these results suggest UniRep is a rich and robust basis for protein engineering prediction tasks beyond those examined here. As examples, a tSNE projection of average UniRep representations for model organism proteomes showed meaningful organism clusters at different phylogenetic levels, and these organism relationships are maintained at the individual protein level. Further, the trained UniRep model is able to partition structurally similar sequences that share little sequence identity, and enable unsupervised clustering of homologous sequences. For instance, UniRep separates proteins from various Structural Classification of Proteins (SCOP) classes derived from crystallographic data. Further, through the use of a top model with the UniRep model (e.g., a simple Random Forest Model trained on top of UniRep), unseen proteins may also be grouped into SCOP superfamily and fold classes, among other examples. Interrogation of the trained UniRep model may also reveal correlations of the internal hidden states in the model with protein secondary structure. For instance, a single neuron in UniRep may be found to discriminate beta sheets from alpha helices, positively correlating with alpha-helix annotations (Pearson's $r=0.33$, $p<1e-5$), and negatively correlating with beta-sheet annotations (Pearson's $r=-0.35$, $p<2e-6$). A larger-scale spatial analysis performed across many helices and sheets from different proteins may reveal an activation pattern of the helix-sheet neuron that indicated it encodes subtle features of both secondary structure units, going beyond individual amino acids. Other example neuron correlations with biophysical parameters may exist, such as solvent accessibility, with UniRep providing a vector space that is semantically rich, encoding structural, evolutionary, and functional information.

The trained UniRep model may be utilized in a variety of different application and may be paired with a variety of different top models. For instance, top models embodied as simple sparse linear models or other model (e.g., Doc2Vec, bag-of-words, etc.) trained on top of UniRep may generate stability prediction results for protein sequence inputs. Protein stability is a fundamental determinant of protein function and a critical engineering endpoint that affects the production yields, reaction rates, and shelf-life of protein catalysts, sensors, and therapeutics. As another example, the UniRep model may enable prediction of the functional effects of single mutations for diverse proteins with distinct functions. For instance, such prediction may be performed using a sparse linear top model trained on UniRep representations to predict the normalized (to wildtype) quantitative function of held out mutants, among other example implementations.

As another example, the trained UniRep model may enable generalization through accurate approximation of the fitness landscape. A core challenge of rational protein engineering is building models which generalize from local data to distant regions of sequence space where more functional variants exist. Deep learning models often have difficulty generalizing outside of their training domain. Unlike traditional models, which are only trained with data specific to the task at hand, UniRep is trained in an unsupervised manner on a wide sampling of proteins and may be utilized to capture general features of protein fitness landscapes which extend beyond task-specific training data. In some implementations, simple linear regression top models may be utilized as the top model to perform the prediction, among other possible implementations. Additionally, the UniRep model may be utilized to assist with the discovery functional diversity and function optimization—the ultimate goals of any protein engineering effort. For instance, the UniRep model may be used (together with an appropriate top model) to solve a sequence prioritization problem to prioritize certain homologs from a generalization set over a various sequence containing varying numbers of mutations relative to a member of the generalization set. In one example, to utilize the UniRep model for function prediction for protein engineering, the same weights learned by UniRep may be loaded, with the final layer being replaced, which previously predicted the next character, with a randomly initialized feed-forward layer with a single output and no non-linearity. For instance, the models can be trained with low learning rate (0.00001), 128 batch size, and only partially feeding forward along the sequence, stopping prediction after 280 Amino Acids, with full back propagation rather than truncated as during the UniRef50 training process. Such an implementation may be utilized to fit the unrolled recurrent computational graph into GPU memory.

As discussed above, an unsupervised representation model utilized in the solutions discussed herein, may be implemented as a Recurrent Neural Networks (RNN) model (e.g., mLSTEM, LSTM, or Gated Recurrent Unit (GRU) model) to achieve protein representation learning. Unlike other models representing proteins, for instance, as one-hot-encoded matrices, RNNs produce fixed-length representations for arbitrary-length proteins by extracting the hidden state passed forward along a sequence. While padding to the maximum sequence length can in principle mitigate the problem of variable length sequences in a one hot encoding, it is ad-hoc, can add artifacts to training, wastes computation processing padding characters, and provides no additional information to a top model besides the naive sequence. Furthermore, even very large representations, like the 1900-dimensional UniRep, are more compact than average protein length 1-hot encodings, reducing the potential for overfitting.

In some example implementations, an mLSTM-based representation model may be utilized for large-scale training runs, such as a large multi-dimensional single layer multiplicative LSTM (e.g., 1900-dimensional with ~18.2 million parameters), a 4-layer stacked mLSTM (e.g., of 256 dimensions per layer (~1.8 million parameters) or a 4-layer stacked mLSTM with 64 dimensions per layer (~0.15 million parameters)), among other examples, regularized with weight normalization. Because all of these networks are recurrent, even the single hidden layer mLSTM is considered "deep" because the network is unrolled in the timestep dimension as a composition of hidden layers through time. In some implementations, it may be assumed that, for large data sets like protein sequence databases or libraries, more expressive models will learn richer representations. Thus, the mLSTM model may be selected to maximize dimensionality to the constraints of the hardware of the computing system executing the model (e.g., mLSTEM-1900 dimensions may be selected in one example as the large single-layer mLSTM because it was approximately the largest dimensionality that could fit in GPU memory).

In one example implementation, sequences of amino acids are one-hot encoded and passed through a 10 dimensional amino-acid character embedding before being input to the mLSTM layer. For the smaller stacked networks, both standard recurrent and residual recurrent connections, in which the hidden states of each layer are summed, are evaluated. For these stacked networks, dropout probability is selected from {0, 0.5}. Hyperparameters are tuned manually on a small number of weight updates and final parameters were selected based on the rate and stability of generalization loss decrease. In some instances, dropout and residual connections both increased validation set error. Accordingly, residual connections, which should improve gradient flow to earlier layers, may not be advantageous here given the small number of layers tested. Additionally, dropout or other regularization outside of weight normalization may also be omitted in some instances because of the high ratio of observations to model parameters, among other example features.

In some implementations, an optimizer may be utilized in the training of the unsupervised representation model. For instance, the model may be trained with the Adam optimizer using truncated-backpropagation through time with initial states initialized to zero at the beginning of sequences and persistent across updates to simulate full backpropagation. Batch sizes and truncation windows may be selected to fit into GPU memory (e.g., 256 and 128 (mLSTM-1900), 512 and 384 (4×-mLSTM-256), 1028 and 384 (4×-mLSTM-64)). Training may be performed using data parallelism on GPUs (e.g., four Nvidia K-80 GPUs (mLSTM-1900) or two Nvidia K-40s (4×-mLSTM-256, 4×-mLSTM-64)), among other example implementations.

Public protein databases, unlike many Natural Language datasets, contain random deleterious mutations yet to be eliminated by selection, and hard-to-catch sequencing/assembly mistakes, both leading to increased noise. In some implementations, a dehomologized" data set (e.g., Uni-Ref50) may be used as a training dataset, such that any two sequences have at most 50% identity with each other. By selecting the single highest quality sequence for each cluster of homologs, such a dataset may be assumed to be less noisy. For instance, UniRef50 contains ~27 million protein sequences. In one example, proteins longer than 2000 amino acids and records containing non-canonical amino acid symbols (X, B, Z, J), and randomly selected test and validation subsets for monitoring training (1% of the overall dataset each) may be removed, with the rest of the data (e.g., ~24 million sequences) used in training.

The mLSTM architecture has two internal states that encode information about the sequence it is processing, the hidden state and the cell state. One hidden state and one cell state are produced for every amino acid in a forward pass over a sequence. Compared to natural language, the complexity of protein folding is assumed to generate more long-range and higher-order dependencies between amino acids. Accordingly, the representation model's representation may be constructed as the average of the model's (e.g., 1900-unit) hidden states, integrating information across distant amino-acids to better represent long-term dependencies critical to protein function prediction. This average hidden state may thereby embody the vector representation generated using the mLSTM-based model. In other implementations, vector representations of the model may be generated from the final hidden state produced by the model when predicting the last amino acid in a protein sequence (Final Hidden) and the last internal cell state (Final Cell). In still other implementations, the representation may be constructed from a concatenation (or Fusion) of all three representation options (e.g., Average Hidden, Final Hidden and Final Cell), among other example implementations. In some instances, a representation such as Average Hidden may be considered the most information-dense representation evaluated here, while Fusion is the most complete. Accordingly, by virtue of its smaller dimensionality, an example such as Average Hidden should be deployed where computational resources are constrained, while the Fusion representation is used for supervised prediction tasks (e.g., of protein stability, biophysical characteristics and function), among other examples.

Any suitable computing device can be used to implement the computing devices and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 600 is depicted in FIG. 6. The computing device 600 is merely an illustrative example of a suitable computing environment and in no way limits the scope of the present disclosure. A "computing device," as represented by FIG. 6, can include a "workstation," a "server," a "laptop," a "desktop," a "hand-held device," a "mobile device," a "tablet computer," or other computing devices, as would be understood by those of skill in the art. Given that the computing device 600 is depicted for illustrative purposes, example embodiments may utilize any number of computing devices 600 in any number of different ways to implement a single embodiment. Accordingly, example embodiments are not limited to a single computing device 600, as would be appreciated by one with skill in the art, nor are they limited to a single type of implementation or configuration of the example computing device 600.

The computing device 600 can include a bus 610 that can be coupled to one or more of the following illustrative components, directly or indirectly: a memory 612, one or more processors 614, one or more presentation components 616, input/output ports 618, input/output components 620, and a power supply 624. One of skill in the art will appreciate that the bus 610 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 6 is merely illustrative of an exemplary computing device that can be used to implement one or more embodiments of the present disclosure, and in no way limits the scope of this disclosure.

The computing device 600 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 600.

The memory 612 can include computer-storage media in the form of volatile and/or nonvolatile memory. The memory 612 may be removable, non-removable, or any combination thereof. Exemplary hardware devices are devices such as hard drives, solid-state memory, optical-disc drives, and the like. Memory 612 can store machine-readable instructions to implement logic to perform one or more tasks using machine learning models, such as described herein. Memory 612 may likewise store data embodying or defining such machine learning models, as well as data to be provided as an input to the models or data representing results or outputs of the models, among other examples. The computing device 600 can include one or more processors that read data from components such as the memory 612, the various I/O components 616, etc. Presentation component(s) 616 present data indications to a user or other device. Exemplary presentation components include a display device, speaker, printing component, vibrating component, etc.

The I/O ports 618 can enable the computing device 600 to be logically coupled to other devices, such as I/O components 620. Some of the I/O components 620 can be built into the computing device 600. Examples of such I/O components 620 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present solutions and embodiments will be apparent to those skilled in the art in view of the foregoing description. Accordingly, this description is to be construed as illustrative only and is for the purpose of teaching those skilled in the art the best mode for carrying out the same. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the general principles discussed herein. It is intended that the present disclosure and inventions discussed herein be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method comprising:
   loading a dataset describing a collection of proteins, wherein the dataset further comprises, for each protein, a respective value of a characteristic of interest;
   providing the dataset as one or more inputs to a trained unsupervised representation model to cause the trained unsupervised representation model to generate a representation for each protein in the collection wherein the trained unsupervised representation model is fine-tuned on related subsets of protein sequences;
   inputting the representation for each protein into a supervised top model to train the supervised top model to obtain a predicted characteristic; and
   using the trained supervised top model to obtain a predicted characteristic for a particular protein.

2. The method of claim 1, further comprising training an unsupervised representation model to generate the trained unsupervised representation model.

3. The method of claim 1, further comprising training a combination of the trained unsupervised representation model and the supervised top model using a particular dataset, wherein loss at the supervised model is backpropagated to at least some of the parameters of the trained unsupervised representation model, wherein the trained unsupervised representation model and the supervised top model are used following training to obtain the predicted characteristic for a protein.

4. The method of claim 1, further comprising:
   accessing a library of protein sequence data corresponding to a plurality of proteins;
   using the trained unsupervised representation model to predict the value of a characteristic or function of interest for each the proteins in the library; and
   using the predicted characteristic for prioritizing proteins from the library based on the predicted values.

5. The method of claim 1, wherein the trained unsupervised representation model comprises a recurrent neural network (RNN) model.

6. The method of claim 5, wherein the RNN comprises a multiplicative long short-term memory network (mLSTM) model.

7. The method of claim 1, further comprising:
   accessing a definition of a particular amino acid;
   initializing a model comprising the trained unsupervised representation model using the definition of the particular amino acid; and
   using the model to predict a next amino acid in an autoregressive manner until a condition is reached.

8. The method of claim 7, wherein the particular amino acid is a random amino acid.

9. The method of claim 7, wherein the model comprises further comprises the top model.

10. The method of claim 1, further comprising:
    accessing a definition of a space of possible protein sequences; and
    iteratively using a trained model to predict a characteristic or function for a subset of proteins in the space based on a search algorithm, wherein the model comprises the trained unsupervised representation model and the top model.

11. The method of claim 1, wherein the top model comprises one of a sparse linear regression model or random forest model.

12. At least one non-transitory machine-readable storage medium with instructions stored thereon, the instruction executable by a machine to cause the machine to:
    load a dataset describing a collection of proteins, wherein the dataset further comprises, for each protein, a respective value of a characteristic of interest;
    provide the dataset as one or more inputs to a trained unsupervised representation model to cause the trained unsupervised representation model to generate a representation for each protein in the collection wherein the trained unsupervised representation model is fine-tuned on related subsets of protein sequences;
    input the representation for each protein into a supervised top model to train the supervised top model to obtain a predicted characteristic; and
    use the trained supervised top model to obtain a predicted characteristic for a particular protein.

13. The storage medium of claim 12, further comprising a model trainer to train the unsupervised representation model using a training data set comprising a collection of protein sequences.

14. The storage medium of claim 12, wherein the representation comprises a fixed length vector representation.

15. The storage medium of claim 12, wherein the unsupervised representation model comprises a multiplicative long short-term memory network (mLSTM) model.

16. A system comprising:
    a processor device;
    a memory;
    a trained unsupervised representation model;
    a supervised top model; and
    logic executable by the processor device to:
        load a dataset describing a collection of proteins, wherein the dataset further comprises, for each protein, a respective value of a characteristic of interest;
        provide the dataset as one or more inputs to a trained unsupervised representation model to cause the trained unsupervised representation model to generate a representation for each protein in the collection wherein the trained unsupervised representation model is fine-tuned on related subsets of protein sequences;
        input the representation for each protein into a supervised top model to train the supervised top model to obtain a predicted characteristic; and
        use the trained supervised top model to obtain a predicted characteristic for a particular protein.

17. The system of claim 16, further comprising a model trainer to train the unsupervised representation model using a training data set comprising a collection of protein sequences.

18. The system of claim 16, wherein the representation comprises a fixed length vector representation.

19. The system of claim 16, wherein the unsupervised representation model comprises a multiplicative long short-term memory network (mLSTM) model.

20. The system of claim 16, further comprising a library of protein sequence data corresponding to a plurality of proteins, wherein the logic is further executable to:
    use the trained unsupervised representation model to predict the value of a characteristic or function of interest for each the proteins in the library; and
    use the predicted characteristic for prioritizing proteins from the library based on the predicted values.

* * * * *